United States Patent
Conrad et al.

[11] Patent Number: 5,917,050
[45] Date of Patent: Jun. 29, 1999

[54] PROCESS FOR PREPARING ALKOXYTRIAZOLINONES

[75] Inventors: Michael Conrad; Reinhard Lantzsch, both of Wuppertal, Germany; Vijay C. Desai; Shekhar V. Kulkarni, both of Shawnee, Kans.

[73] Assignees: Bayer Corporation, Pittsburgh, Pa.; Bayer Aktiengesellschaft, Leverkusen, Germany

[21] Appl. No.: 09/022,262

[22] Filed: Feb. 11, 1998

[51] Int. Cl.$^6$ .................................................. C07D 249/12
[52] U.S. Cl. .......................................................... 548/263.6
[58] Field of Search ........................................... 548/263.6

[56] References Cited

U.S. PATENT DOCUMENTS 5,599,945  2/1997  Wroblowsky et al. ............... 548/263.6

OTHER PUBLICATIONS

J. Chem. Soc. Perkin I, (month unavailable) 1973, pp. 2644–2646.
Arch. Pharm. 307 (month unavailable) 1974, pp. 889–891.

*Primary Examiner*—Patricia L. Morris
*Attorney, Agent, or Firm*—Joseph C. Gil; Carol Marmo

[57] ABSTRACT

Alkoxytriazolinones of the formula (I) [known for example as intermediates for preparing agrochemically active compounds]

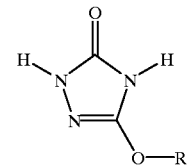

(I)

wherein R represents an alkyl group, an alkenyl group, an alkinyl group, a cycloalkyl group, a cycloalkylalkyl group, an aryl group or an arylalkyl group, any of which may be substituted, are prepared by reacting a) thioimidodicarboxylic diesters of the general formula (II)

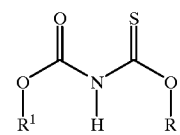

(II)

wherein R is as defined above and $R^1$ represents an alkyl group, an arylalkyl group or an aryl group, any of which may be substituted, with b) hydrazine, hydrazine hydrate or an acid adduct of hydrazine.

The reaction is conducted i) in the presence of a diluent and, optionally, in the presence of a basic reaction auxiliary, and ii) at temperatures between −10° C. and +100° C.

14 Claims, No Drawings

PROCESS FOR PREPARING ALKOXYTRIAZOLINONES

BACKGROUND OF THE INVENTION

The present invention relates to a novel process for preparing alkoxytriazolinones, most of which are known and which can be used as intermediates for preparing agrochemically active compounds.

Alkoxytriazolinones and a plurality of methods for their preparation are known and described in the literature.

Thus, for example, the compound 5-methoxy-2,4-dihydro-3H-1,2,4-triazol-3-one (or 3-methoxy-1,2,4-triazol-5(4H)-one) is obtained when the compound ethyl (methoxy-methylsulfanyl-methylene)-carbamidate (or ethyl N-[methoxy-(methylthio)methylene]carbamate) is refluxed with hydrazine hydrate in ethanol (cf. J. Chem. Soc. Perkin I 1973, 2644–2646). However, the starting material employed for this purpose is obtained only in unsatisfactory yield, by methylation of methoxythio-carbonylethoxycarbonyl-amine (i.e., ethyl methoxy-(thiocarbonyl)-carbamate or 1-ethyl-3-methyl thioimidodicarboxylate) with dimethyl sulfate.

In the reaction of phenyl cyanate with ethyl carbazate small amounts of the compound 5-ethoxy-2,4-dihydro-3H-1,2,4-triazol-3-one (or 3-ethoxy-$\Delta^3$-1,2,4-triazolin-5-one) are formed (cf. Arch. Pharm. 307 (1974), 889–891). However, the use of this reaction for specifically preparing alkoxytriazolinones has not been disclosed.

A further method for preparing alkoxytriazolinones comprises reacting iminocarbonic diesters with carbazinic esters to give N'-(amino-alkoxy-methylene)-hydrazine-carboxylic esters ("semicarbazide derivatives"), and condensing these intermediates to the corresponding alkoxytriazolinones (cf. U.S. Pat. No. 5,599,945). This preparation route likewise often provides only unsatisfactory yields of alkoxytriazolinones.

DESCRIPTION OF THE INVENTION

It has now been found that alkoxytriazolinones of the general formula (I)

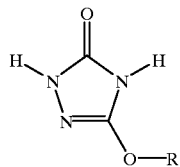

(I)

(wherein R represents an alkyl group, an alkenyl group, an alkinyl group, a cycloalkyl group, a cycloalkylalkyl group, an aryl group or an arylalkyl group, any of which may be substituted) are obtained in very good yields and in high purity by a process comprising reacting a) thioimidodicarboxylic diesters of the general formula (II)

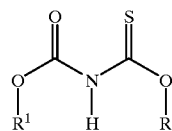

(II)

(wherein R is as defined above and R represents an alkyl group, an arylalkyl group or an aryl group, any of which may be substituted) with b) hydrazine, hydrazine hydrate or an acid adduct of hydrazine, with said reaction being conducted i) in the presence of a diluent and, optionally, in the presence of a basic reaction auxiliary, and ii) at temperatures between –10° C. and +100° C.

Surprisingly, the alkoxytriazolinones of the general formula (I) can be obtained in very good yields and in high purity by the process according to the invention. It is particularly surprising and was unforeseeable for a person skilled in the art that the "cyclocondensation" of the compounds of the general formula (II) to the compounds of the general formula (I) proceeds with such high regioselectivity, i.e. that the ring closure to 5-thioxo-[1,2,4]-triazolidin-3-one, which was to be expected at least as a "side reaction", can be avoided.

Compared with the prior art noted above, the process according to the invention has the advantage that an alkylation step in the preparation of the precursors is unnecessary and the use of industrially unfavorable precursors (such as the unstable iminocarbonic diesters) can be avoided. Moreover, the starting materials of the general formula (II) are products which can be prepared cost-effectively in a relatively simple manner. The process according to the invention is therefore a useful advance over the prior art.

The invention preferably relates to the preparation of compounds of the formula (I), in which R represents i) an alkyl group, an alkenyl group or an alkinyl group having in each case up to 6 carbon atoms, and any one of which group may be cyano-, halogen- or $C_1$–$C_4$-alkoxy-substituted, or ii) a cycloalkyl group having 3 to 6 carbon atoms or a cycloalkylalkyl group having 3 to 6 carbon atoms in the cycloalkyl moiety and 1 to 4 carbon atoms in the alkyl moiety, either of which groups may be halogen- or $C_1$–$C_4$-alkyl-substituted, or iii) an aryl group having 6 or 10 carbon atoms or an arylalkyl group having in 6 or 10 carbon atoms in the aryl moiety and 1 to 4 carbon atoms in the alkyl moiety, either of which groups may be cyano-, halogen-, $C_1$–$C_4$-alkyl-, $C_1$–$C_4$- halogenoalkyl-, $C_1$–$C_4$-alkoxy-, $C_1$–$C_4$-halogenoalkoxy- or $C_1$–$C_4$-alkoxy-carbonyl-substituted.

The invention more preferably relates to the preparation of compounds of the formula (I), in which R represents i) methyl, ethyl, n- or i-propyl, n-, i- or s-butyl, any of which may be cyano-, fluorine-, chlorine- and/or bromine-, methoxy- or ethoxy-substituted, or ii) propenyl, butenyl, propinyl or butinyl, any of which may be cyano-, fluorine-, chlorine- and/or bromine-substituted, iii) cyclopropyl or cyclopropylmethyl, either of which may be fluorine-, chlorine-, methyl- or ethyl-substituted or iv) phenyl or benzyl, either of which may be cyano-, fluorine-, chlorine-, bromine-, methyl-, ethyl-, trifluoromethyl-, methoxy-, ethoxy-, difluoromethoxy-, trifluoromethoxy-, methoxycarbonyl- or ethoxycarbonyl-substituted.

Most preferably, the invention relates to the preparation of compounds of the formula (I) in which R represents methyl, ethyl, n- or i-propyl.

Using, for example, 1,3-diethyl thioimidodicarboxylate and hydrazine as starting materials, the course of the reaction in the process according to the invention can be illustrated by the following scheme:

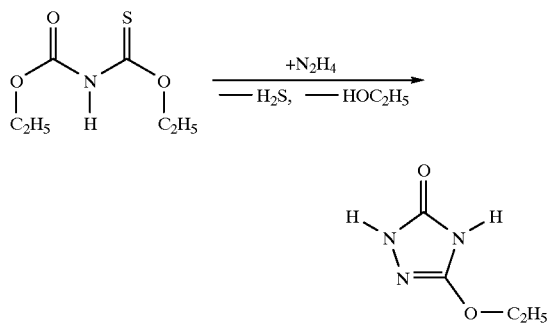

Formula (II) provides a general definition of the thioimido-dicarboxylic diesters to be used as starting materials in the process according to the invention for preparing compounds of the formula (I). In the formula (II), R preferably and most preferably has the same meaning as with the preferred and most preferred definitions for the compounds of the formula (I). $R^1$ preferably represents an alkyl group having 1 to 4 carbon atoms, a benzyl group or a phenyl group, and most preferably a methyl or ethyl group.

The starting materials of the general formula (II) are known and/or can be prepared by processes known per se (cf. Chem. Pharm. Bull. 20 (1972), 2618–2625; J. Chem. Soc. Perkin 1 1973, 2644–2646; Chem. Ber. 114 (1981), 2075–2086; German patent 3,010,204).

The process according to the invention is carried out using hydrazine, hydrazine hydrate or an acid adduct of hydrazine. Examples of acid adducts of hydrazine include hydrazine acetate, hydrazine hydrochloride and hydrazine sulfate. However, preference is given to using hydrazine hydrate as the starting material in the process according to the invention.

The process according to the invention for preparing alkoxy-triazolinones of the general formula (I) is carried out using a diluent. Suitable diluents for carrying out the process according to the invention are in particular inert organic solvents. These include in particular aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or butyronitrile; amides such as N,N-dimethylformamide, N,N-dimethylacetamide, dimethylacetamide, N-methylformanilide, N-methyl-pyrrolidone or hexamethylphosphoric triamide; esters such as methyl acetate or ethyl acetate; sulfoxides such as dimethyl sulfoxide; alcohols such as methanol, ethanol, n- or i-propanol, n-, i-, s- or t-butanol, ethylene glycol monomethyl ether, ethylene glycol monoethyl ether, diethylene glycol monomethyl ether, diethylene glycol monoethyl ether, mixtures thereof with water or pure water.

Preferred diluents in the process according to the invention are alcohols such as, in particular, methanol, ethanol, n- and i-propanol.

It has been found that the yield of the product can be significantly increased by controlling the pH. Preferably the pH is kept between 6 and 11, more preferably between 7 and 10 and most preferably between 8 and 9. The pH can be controlled by several methods. For example, the materials can be added at such a rate as to maintain the pH within the above identified range. Alternatively, a basic reaction auxiliary can be added. Suitable basic reaction auxiliaries for the process according to the invention are generally the customary inorganic or organic bases or acid acceptors. These include preferably alkali metal or alkaline earth metal acetates, amides, carbonates, bicarbonates, hydrides, hydroxides or alkoxides such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide; furthermore also basic organic nitrogen compounds such as, for example, trimethylamine, triethylamine, tripropylamine, tributylamine, ethyl diisopropylamine, N,N-dimethylcyclohexylamine, dicyclohexylamine, ethyl-dicyclohexylamine, N,N-dimethyl-aniline, N,N-dimethylbenzylamine, pyridine,2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diaza-bicyclo[4.3.0]-non-5-ene (DBN), or 1,8-diazabicyclo[5.4.0]-undec-7-ene (DBU).

Most preferred basic reaction auxiliaries for the process according to the invention are alkali metal hydroxides or alkali metal alkoxides such as, in particular, sodium hydroxide or potassium hydroxide, sodium methoxide or potassium methoxide, sodium ethoxide or potassium ethoxide.

In the practice of the process according to the invention, the reaction temperatures can be varied within a relatively wide range. In general, the process is carried out at temperatures between −10° C. and 100° C., and preferably between −5° C. and +80° C.

The process according to the invention is generally carried out at atmospheric pressure. However, it is also possible to carry out the process according to the invention under elevated or reduced pressure—in general between 0.1 bar and 10 bar.

In the practice of the process according to the invention, in general 1.0 to 1.5 mol, preferably 1.05 to 1.20 mol, of hydrazine, hydrazine hydrate or hydrazine acid adduct, and, when used, from 0.001 to 1.5 mol, preferably 0.05 to 1.0 mol, of basic reaction auxiliary are employed per mole of thioimidodicarboxylic diester of the formula (II).

In one preferred embodiment of the process according to the invention, the starting material of the general formula (II) is initially charged in a diluent and the hydrazine, hydrazine hydrate or hydrazine acid adduct and the basic reaction auxiliary—preferably in a diluent—are slowly added. The reaction mixture is then stirred until the reaction has ended and subsequently worked up by customary methods or else employed without any further purification for further reactions (cf. U.S. Pat. No. 5,599,945).

The alkoxytriazolinones of the general formula (I) to be prepared by the process according to the invention can be employed as intermediates in the preparation of herbicidally active compounds (cf. U.S. Pat. Nos. 5,599,945, 5,057,144 and 5,534,486).

The invention is further illustrated but is not intended to be limited by the following examples in which all parts and percentages are by weight unless otherwise specified.

PREPARATION EXAMPLES

Example 1

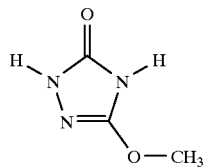

14.5 g (94 mmol) of 1,3-dimethyl thioimidodicarboxylate were initially charged in 55 ml of methanol and cooled to 0° C. At this temperature, a solution of 5.08 g (102 mmol) of hydrazine hydrate and 0.61 g (9.4 mmol) of potassium hydroxide in 25 ml of methanol was added dropwise with stirring over a period of one hour. The cooling bath was removed and the reaction mixture was stirred for approximately 5 hours at room temperature (about 20° C.). The solvent was then carefully distilled off using waterpump vacuum.

9.84 g (91% of theory) of 5-methoxy-2,4-dihydro-3H-1,2,4-triazol-3-one was obtained as crude product.

Example 2

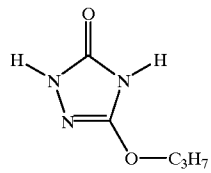

17.2 g (94 mmol) of 1-methyl-3-propyl thioimidodicarboxylate were initially charged in 55 ml of methanol and cooled to 0° C. At this temperature, a solution of 5.08 g (102 mmol) of hydrazine hydrate and 0.61 g (9.4 mmol) of potassium hydroxide in 25 ml of methanol were added dropwise with stirring over a period of one hour. The cooling bath was removed and the reaction mixture was stirred for approximately 5 hours at room temperature (about 20° C.). The solvent was then carefully distilled off using waterpump vacuum.

12.37 g (92% of theory) of 5-propoxy-2,4-dihydro-3H-1,2,4-triazol-3-one was obtained as crude product.

Example 3

14.5 g (94 mmol, 96.6% pure) of 1,3-dimethyl thioimidodicarboxylate and 0.305 g (4.7 mmol, 87% pure) of potassium hydroxide were initially charged in 55 ml of methanol and cooled to 0° C. At this temperature, a solution of 5.08 g (102 mmol) of hydrazine hydrate in 25 ml of methanol was added at such a rate as to maintain the pH between 8 and 9. The addition took about 2 hours. The cooling bath was removed and the reaction mixture was stirred for about 5 hours at room temperature (about 20° C.).

10.93 g (90% pure, i.e., 91% of theory) of 5-methoxy-2,4-dihydro-3H-1,2,4-triazol-3-one was obtained as crude product.

Example 4

14.5 g (94 mmol, 96.6% pure) of 1,3-dimethyl thioimidodicarboxylate were initially charged in 55 ml of methanol and cooled to 0° C. At this temperature, a solution of 5.08 g (102 mmol) of hydrazine hydrate in 25 ml of methanol was added with stirring over a period of thirty minutes. Due to the faster rate of addition, the pH remained between 8 and 9. The cooling bath was removed and the reaction mixture was stirred for approximately 5 hours at room temperature (about 20° C.). The solvent was then carefully distilled off using waterpump vacuum.

10.56 g (87% pure, i.e., 85% of theory) of 5-methoxy-2,4-dihydro-3H-1,2,4-triazol-3-one was obtained as crude product.

Example 5

18.96 g (105 mmol, 98% pure) of 1-methyl-3-propyl thioimido-dicarboxylate and 0.338 g (5.25 mmol, 87% pure) of potassium hydroxide were initially charged in 55 ml of methanol and cooled to 0° C. At this temperature, a solution of 5.50 g (112 mmol) of hydrazine hydrate in 25 ml of methanol was added at such a rate as to maintain the pH between 8 and 9. The addition took about 2 hours. The cooling bath was removed and the reaction mixture was stirred for about 5 hours at room temperature (about 20° C.).

15.18 g (91% pure, i.e., 92% of theory) of 5-propoxy-2,4-dihydro-3H-1,2,4-triazol-3-one was obtained as crude product.

Example 6

18.96 g (105 mmol, 98% pure) of 1-methyl-3-propyl thioimido-dicarboxylate were initially charged in 55 ml of methanol and cooled to 0° C. At this temperature, a solution of 5.50 g (110 mmol) of hydrazine hydrate in 25 ml of methanol was added with stirring over a period of thirty minutes. Due to the faster rate of addition, the pH remained between 8 and 9. The cooling bath was removed and the reaction mixture was stirred for approximately 5 hours at room temperature (about 20° C.). The solvent was then carefully distilled off using waterpump vacuum.

14.63 g (90% pure, i.e., 87.7 of theory) of 5-propoxy-2,4-dihydro-3H-1,2,4-triazol-3-one was obtained as crude product.

Starting materials of the formula (II):

Example (II-1)

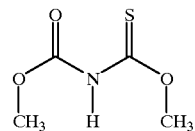

8.3 g (100 mmol) of sodium thiocyanate and 0.4 g (3 mmol) of quinoline were initially charged in 50 ml of methyl isobutyl ketone. At room temperature (about 20° C.), 10.2 g (107 mmol) of methyl chloroformate were added dropwise with stirring over a period of about 45 minutes, and the reaction mixture was stirred at room temperature for three hours. After the addition of 6.4 g (200 mmol) of methanol (over a period of 30 minutes), the mixture was stirred at room temperature for a further 16 hours. 30 ml of water and 3 ml of concentrated hydrochloric acid were added. The organic phase was separated off and the aqueous phase was extracted two more times with methyl isobutyl ketone. The combined organic phases were washed with 20 ml of water, dried with magnesium sulfate and filtered. The solvent was carefully distilled off from the filtrate using waterpump vacuum.

14.5 g (97% of theory) of 1,3-dimethyl thioimidodicarboxylate, which can be used without further purification for the reaction according to Example 1, were obtained.

Example (II-2)

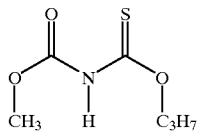

8.3 g (100 mmol) of sodium thiocyanate and 0.4 g (3 mmol) of quinoline were initially charged in 50 ml of methyl isobutyl ketone. At room temperature (about 20° C.), 10.2 g (107 mmol) of methyl chloroformate were added dropwise with stirring over a period of about 45 minutes, and the reaction mixture was stirred at room temperature for three hours. After the addition of 12 g (200 mmol) of n-propanol (over a period of 30 minutes), the mixture was stirred at room temperature for a further 16 hours. 30 ml of water and 3 ml of concentrated hydrochloric acid were added. The organic phase was separated off and the aqueous phase was extracted two more times with methyl isobutyl ketone. The combined organic phases were washed with 20 ml of water, dried with magnesium sulfate and filtered. The solvent was carefully distilled off from the filtrate using waterpump vacuum.

17.2 g (97% of theory) of 1-methyl-3-propyl thioimidodicarboxylate, which can be used without any further purification for the reaction according to Example 2, were obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. A process for preparing alkoxytriazolinones of the general formula (I),

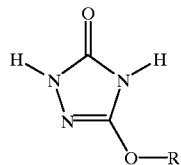

wherein
R represents an alkyl group, an alkenyl group, an alkinyl group, a cycloalkyl group, a cycloalkylalkyl group, an aryl group or an arylalkyl group, any of which may be substituted, comprising reacting
a) thioimidodicarboxylic diesters of the general formula (II)

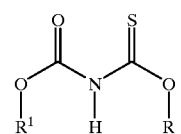

wherein R is as defined above and $R^1$ represents an alkyl group, an arylalkyl group or an aryl group, any of which may be substituted, with
b) hydrazine, hydrazine hydrate or an acid adduct of hydrazine,
with said reaction being conducted i) in the presence of a diluent and, optionally, in the presence of a basic reaction auxiliary, and ii) at temperatures between −10° C. and +100° C.

2. The process of claim 1, wherein R represents
i) an alkyl group, an alkenyl group or an alkinyl group having in each case up to 6 carbon atoms, and any one of which group may be cyano-, halogen- or $C_1$–$C_4$-alkoxy-substituted, or
ii) a cycloalkyl group having 3 to 6 carbon atoms or a cycloalkylalkyl group having 3 to 6 carbon atoms in the cycloalkyl moiety and 1 to 4 carbon atoms in the alkyl moiety, either of which groups may be halogen- or $C_1$–$C_4$-alkyl-substituted, or
iii) an aryl group having 6 or 10 carbon atoms or an arylalkyl group having 6 or 10 carbon atoms in the aryl moiety and 1 to 4 carbon atoms in the alkyl moiety, either of which groups may be cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy- or $C_1$–$C_4$-alkoxy-carbonyl-substituted.

3. The process of claim 1, wherein R represents
i) methyl, ethyl, n- or i-propyl, n-, i- or s-butyl, any of which may be cyano-, fluorine-, chlorine- and/or bromine-, methoxy- or ethoxy-substituted, or
ii) propenyl, butenyl, propinyl or butinyl, any of which may be cyano-, fluorine-, chlorine- and/or bromine-substituted,
iii) cyclopropyl or cyclopropylmethyl, either of which may be fluorine-, chlorine-, methyl- or ethyl-substituted or
iv) phenyl or benzyl, either of which may be cyano-, fluorine-, chlorine-, bromine-, methyl-, ethyl-, trifluoromethyl-, methoxy-, ethoxy-, difluoromethoxy-, trifluoromethoxy-, methoxycarbonyl- or ethoxycarbonyl-substituted.

4. The process of claim 1, wherein R represents methyl, ethyl, n- or i-propyl.

5. The process of claim 1, wherein $R^1$ represents alkyl having 1 to 4 carbon atoms, benzyl or phenyl.

6. The process of claim 1, wherein $R^1$ represents methyl or ethyl.

7. The process of claim 1, wherein the reaction is carried out at temperatures between −5° C. and +80° C.

8. The process of claim 1, wherein the diluent used is an alcohol.

9. The process of claim 1, wherein a basic reaction auxiliary is used and such auxiliary is an alkali metal hydroxide or alkali metal alkoxide.

10. The process of claim 9, wherein the starting material of formula (II) and the basic reaction auxiliary are initially charged in a diluent and the hydrazine, hydrazine hydrate or hydrazine acid adduct are slowly added and the reaction mixture is stirred until the reaction has ended.

11. The process of claim 9, wherein the starting material of the formula (II) is initially charged in a diluent and the hydrazine, hydrazine hydrate or hydrazine acid adduct and the basic reaction auxiliary are slowly added and the reaction mixture is stirred until the reaction has ended.

12. The process of claim 1, wherein the reaction is carried out in a pH range of from 6 to 11.

13. The process of claim 12, wherein the reaction is carried out in a pH range of from 7 to 10.

14. The process of claim 13, wherein the reaction is carried out in a pH range of from 8 to 9.

* * * * *